United States Patent [19]
Merten, Jr.

[11] Patent Number: 5,259,417
[45] Date of Patent: Nov. 9, 1993

[54] DEVICE FOR TESTING CLOSURE DISKS AT HIGH RATES OF CHANGE OF PRESSURE

[75] Inventor: Charles W. Merten, Jr., West Carrollton, Ohio

[73] Assignee: The United States of America as represented by the United States Department of Energy, Washington, D.C.

[21] Appl. No.: 811,211

[22] Filed: Dec. 20, 1991

Related U.S. Application Data

[62] Division of Ser. No. 491,810, Mar. 12, 1990, Pat. No. 5,081,862.

[51] Int. Cl.$^5$ .............................................. C01M 3/04
[52] U.S. Cl. ......................................... 138/89; 138/90; 73/49.8; 220/266
[58] Field of Search .................. 138/89, 89.1-89.4, 138/90; 73/47.1, 47.8, 4 R; 137/68.1; 220/266, 265, 276

[56] References Cited

U.S. PATENT DOCUMENTS

| | | | |
|---|---|---|---|
| 4,382,379 | 5/1983 | Kelly | 73/49.8 |
| 4,452,306 | 6/1984 | Polley | 137/68.1 |
| 4,602,500 | 7/1986 | Kelly | 73/49.8 |
| 4,809,751 | 3/1989 | McKenzie | 73/49.8 |
| 4,899,903 | 2/1990 | Miyasaka et al. | 138/87 |
| 5,024,079 | 6/1991 | Dufort | 73/49.8 |

*Primary Examiner*—Harvey C. Hornsby
*Assistant Examiner*—Patrick F. Brinson
*Attorney, Agent, or Firm*—Luis M. Ortiz; James H. Chafin; William R. Moser

[57] ABSTRACT

A device for testing the burst pressure of closure disks which provides high pressure to both sides of a disk and rapidly releases pressure from one side thereof causing a high rate of change of pressure. A hollow notched plug allows the rapid release of pressure upon rupturing. A means is also disclosed for transmitting a tensile load from a piston to a hollow notched plug and for sealing the means for transmitting load within a hole in a piston.

8 Claims, 4 Drawing Sheets

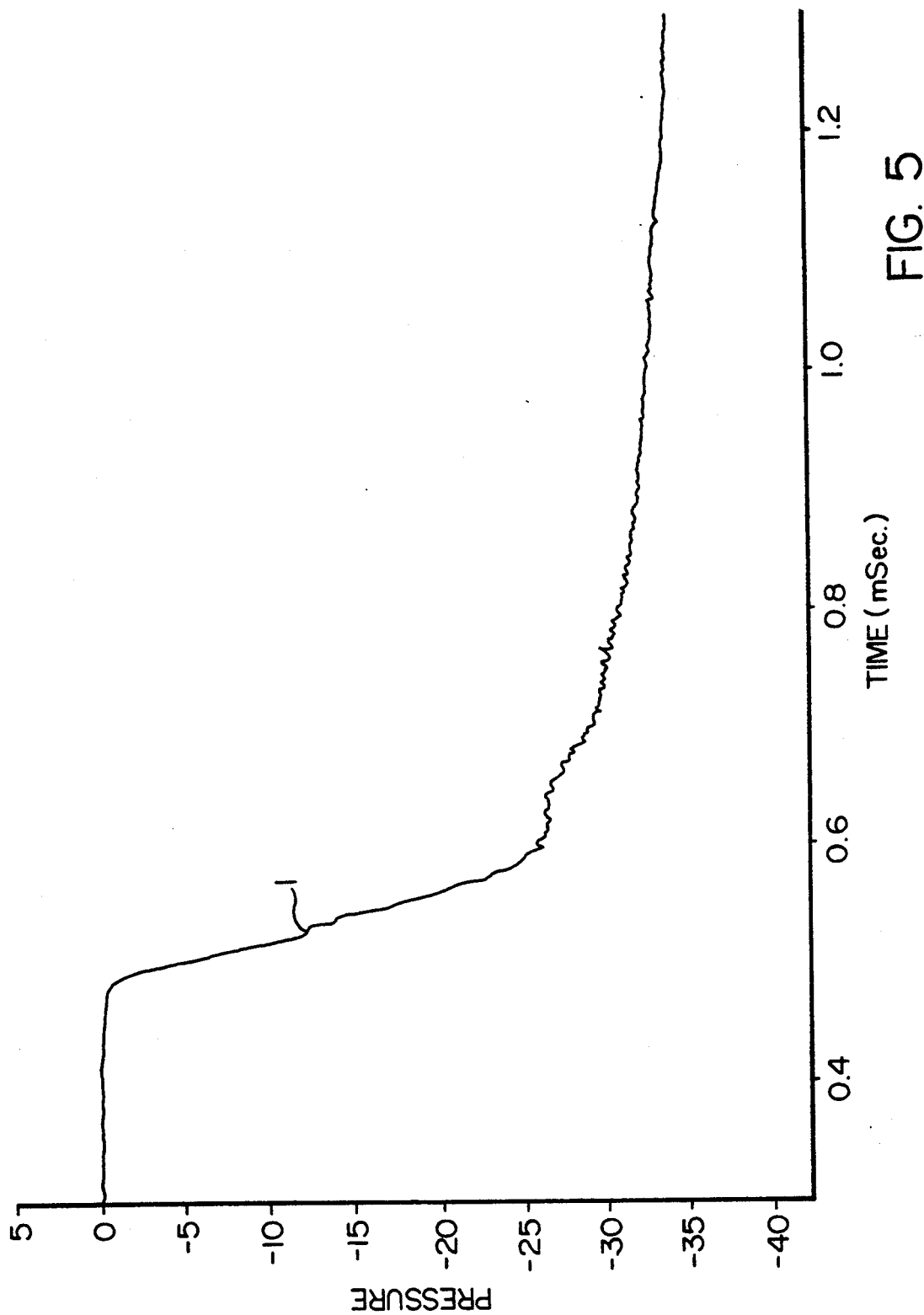

DEVICE FOR TESTING CLOSURE DISKS AT HIGH RATES OF CHANGE OF PRESSURE

The United States Government has rights in this invention pursuant to Contract No. DE-AC04-76DP00053 between the United States Department of Energy and Monsanto Research Corp. (now EG&G Mound Applied Technologies).

This application is a divisional of application Ser. No. 07/491,810, filed Mar. 12, 1990, now U.S. Pat. No. 5,081,862.

BACKGROUND OF THE INVENTION

This invention relates to a method and device for testing the burst pressure of closure disks. Government has rights in this invention pursuant to Contract No. DE-AC04-76DP00053 between the United States Department of Energy and Monsanto Research Corp. (now EG&G Mound Applied Technologies).

Actuators may be viewed as devices which supply short but intense bursts of pressure, whereas igniters supply intense bursts of heat. Actuator and igniter structures are quite similar. Each comprises a header having two or more insulated electrodes electrically connected by a bridgewire. A charge cavity is situated atop the bridgewire surface of the header. The charge cavity may either be integral to the header shell or may comprise a can welded to the top of the header. The charge cavity is filled with pyrotechnic or explosive powder and a closure disk is welded to either the shell or the can to contain the powder and create a hermetic seal. Function times for these devices are thought to be 0.00005 second or less.

Actuators and igniters of this type are primarily used in aerospace applications. Examples include explosive bolts, ejection seats, explosive valves, igniters to start rocket motors, and deployment systems for parachutes. Actuators are also used in air bag restraint systems for automobiles.

Means to produce a rapid release of pressure can be used in other applications as well. For instance, air guns and gas guns may require such a means as well as methods of projecting projectiles by a rapid release of pressure.

A need to test closure disks at high rates of change of pressure exists. It is known that igniters exhibit variable work output upon functioning. It is also known that as pressure of a gas over a pyrotechnic increases, the rate of burn also increases. In addition, the pressure differential at which a closure disk bursts is dependent on the rate of pressurization. Since the burn rate depends upon the pressure differential, it is difficult to test for burst pressure differential of a closure disk by producing pressure using pyrotechnics. A need therefore exists for means of rapidly producing a pressure differential without pyrotechnics.

A hand pump such as a hand-operated hydraulic pump has previously been used to test closure disks. Pressure is applied to a closure disk by means of a hydraulic fluid. Problems exist with the hand pump method of testing in that the minimum time of rupture for closure tests is on the order of several seconds.

Another device which might be used to test closure disks is the gas gun or shock tube, although the inventors have no knowledge of tests having been performed on closure disks with this device. This type of device requires an explosive charge used to drive a piston or flyer down a tube. The piston or flyer compresses gas behind a diaphragm until the diaphragm ruptures resulting in a shock wave. The shock wave travels down the tube creating high pressures and temperatures reaching 2000° C. These instruments usually have lengths of 20 feet or longer and are very expensive. A need therefore exists for a closure disk tester which ruptures a closure disk without requiring lengthy rupture times, high temperatures, or high costs.

SUMMARY OF THE INVENTION

It is an object of the present invention to overcome the problems set forth above.

It is a further object of the present invention to provide a closure disk tester which provides a pressure differential across a closure disk to rupture the disk and detects a rate of change of pressure and pressure differential at the time of rupture.

It is a further object of the present invention to provide a device which accomplishes a high rate of pressure change by producing a rapid venting of high pressure.

It is a further object of the present invention to provide a device for transmission of a tensile load with means providing a seal against the escape of pressure.

These and other objects are achieved by the present invention which, in one aspect, comprises a closure disk tester which utilizes a rapid venting of high pressure to create a pressure differential in order to rupture a closure disk. High pressure is released from one side of the disk through a conduit upon breakage of a hollow notched plug. The plug initially contains high pressure in its hollow cavity on the downstream side of the closure disk and ruptures circumferentially about its notch upon application of an axial load.

Another aspect of the present invention comprises a device which allows the transmission of a tensile load without pressure escape. The device comprises a pressure chamber, a piston forming a face of the pressure chamber and being movable outward with respect to the chamber, attaching means for attaching the piston to a device to which tensile force is to be applied, and drawing means for drawing the piston toward the pressure chamber without rotation of the piston relative to the pressure chamber. The drawing means comprise a sealing means for preventing the escape of pressure through the piston. The device may be mechanically connected to the aforesaid hollow notched plug. The device may be used in the closure disk tester but is not limited to that application.

These and other objects and features of the present invention will be more fully understood with reference to the accompanying drawings and the following description of the embodiments shown in those drawings. The invention is not limited to the exemplary embodiments but should be recognized as contemplating all modifications, additions, substitutions and deletions within the skill of an ordinary artisan.

BRIEF DESCRIPTION OF THE DRAWINGS

FIG. 5 is a graph of pressure drop over time in accordance with a testing method using the device of the present invention.

DETAILED DESCRIPTION OF THE PREFERRED EMBODIMENTS

Figure 1:
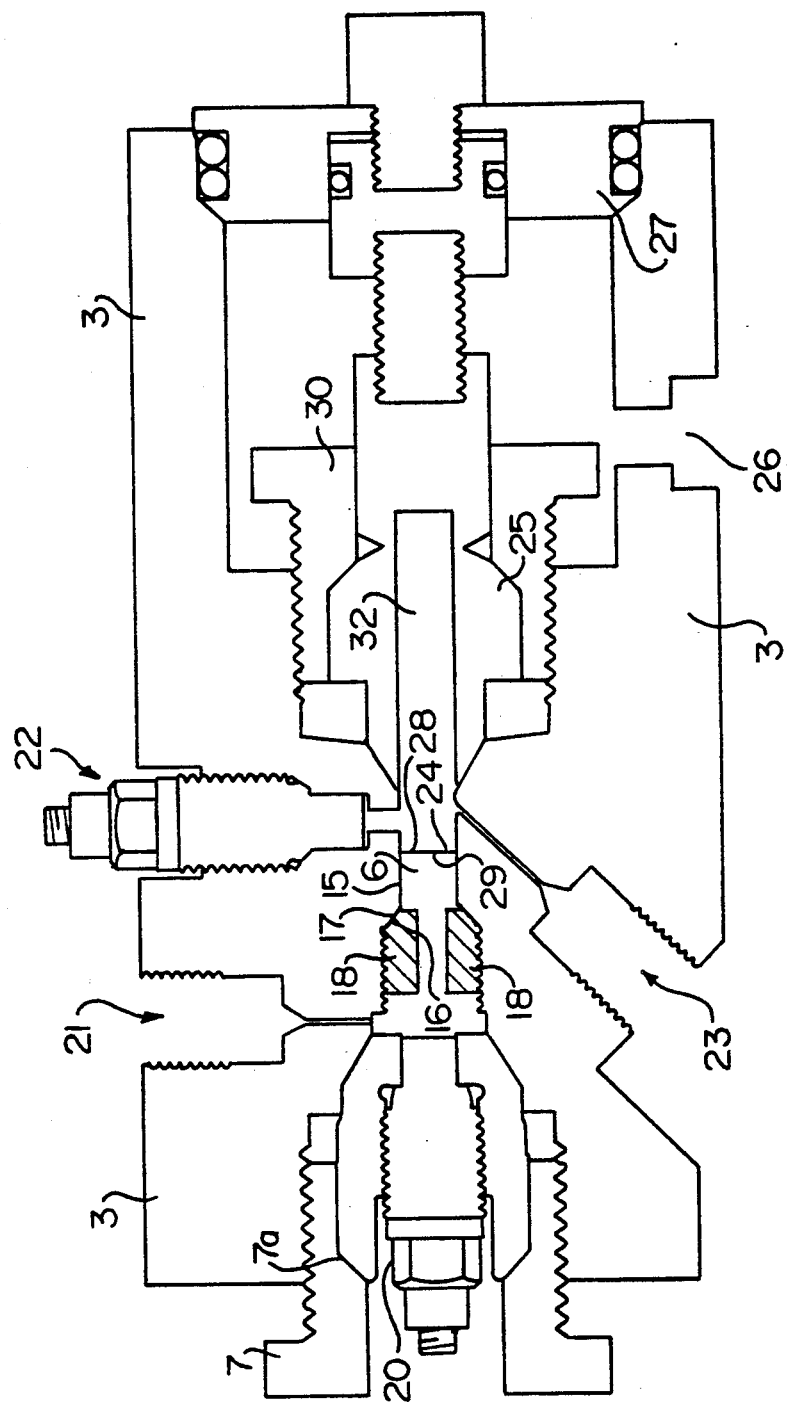
FIG. 1 is a cross-sectional view of a device according to the present invention.

FIG. 1 shows a device according to the present invention used to create a high rate of change of pressure across a closure disk 24. The device comprises a substantially cylindrical body which has been bored by known means to provide a retaining conduit for holding a closure disk and shell assembly. The body is preferably made of metal. As shown in the figures, the body has been bored or die cast to provide high pressure inlets 21 and 23, a receptacle for a transducer 22, a receptacle for a transducer 20, a pressure chamber 43, a low pressure inlet 26, and a receptacle for a gland nut 30 used to retain a hollow notched plug 25 within the device. The pressure chamber 43 is preferably of a cylindrical configuration.

Figure 2:
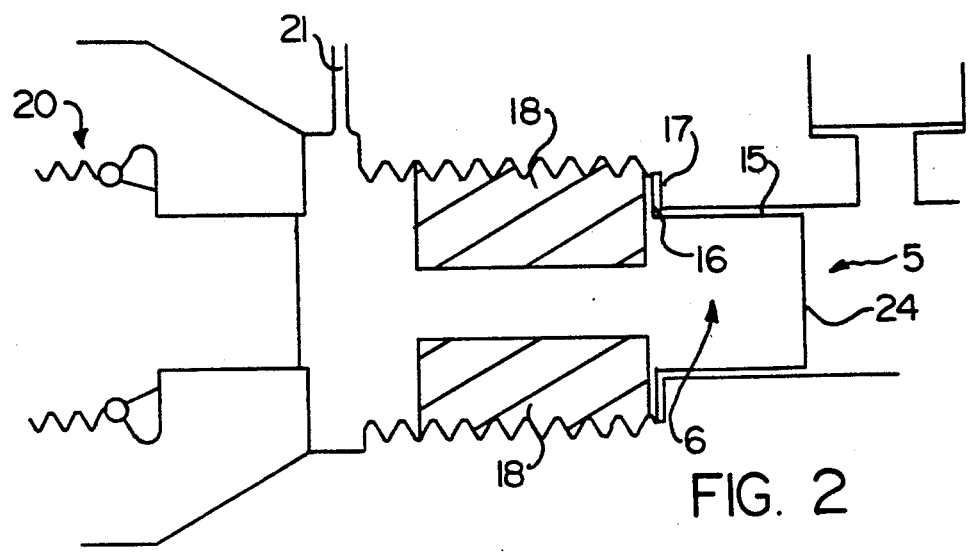
FIG. 2 is a close-up, cross-sectional view of the device of FIG. 1 showing detail of a retaining conduit and a shell an disk assembly.

As shown in the Figures, the closure disk 24 is hermetically sealed to a shell 15. The shell is provided with a flange 16 which seats against a stop 17 on the upstream side of the disk As best seen in FIG. 2, the shell and disk assembly is retained in a retaining conduit 6 by means of a flange 16, on the shell 15, and a stop 17 in the retaining conduit 6. The hollow seating means 18 is preferably threaded and is tightenable to force the flange 16 against the stop 17. High pressure exerted from high pressure inlet 21 through the seating means 18 further forces the flange 16 against the stop 17 to hold the shell and disk assembly 5 securely in place.

When loading a shell and disk assembly 5 having a disk 24 to be tested, the transducer 20 is first removed from the device body 3 providing access to the removable hollow seating means 18. The seating means 18 is then removed to provide access to the retaining conduit 6. A spent shell and disk assembly may need to be removed if left in the retaining conduit 6 from a previous test. Once emptied, the retaining conduit 6 is ready to receive a shell and disk assembly 5 for testing. The assembly 5 is positioned within the retaining conduit 6, the seating means 18 are inserted to press the flange 16 against the stop 17 holding the assembly in place, and the transducer 20 is positioned in its receptacle. The transducer may be held in place by means of a gland nut 7 which may have a tapered edge 7a. A hollow seating means 18 allows passage of fluid therethrough.

High pressure inlets 21 and 23 are connected to high pressure sources which preferably provide pressure to both sides of the closure disk in the range of from 30,000 to 50,000 psi. Pressure is rapidly vented or released from one side of the closure disk by a device of the present invention, as shown more particularly in FIG. 3. Pressure is rapidly vented through a high pressure conduit 32 upon rupture of a hollow notched plug 25 at notch 33. This causes a lower pressure on the downstream side 28 of the closure disk 24 than on the upstream side 29 thereof. The high rate of pressure decrease on the downstream side 28 of the closure disk 24 increases with increasing initial pressure and has the effect of simulating a high rate of pressure increase on the upstream side 29 of the closure disk 24.

The high pressure source may comprise a high pressure pump or a pump and intensifier arrangement. Preferably, the source is connected to both inlets 21 and 23. Valves are used to provide a path of the pressurized gas between the two inlets for equalization. Prior to rupturing the plug 25, a valve is used to isolate the downstream high pressure inlet from the high pressure source and the upstream inlet 21. Preferably the valve is located proximal to the downstream inlet 23 to minimize the volume which gas occupies downstream of the disk 24.

A high-pressure, fast rise-time pressure transducer 22, mounted in a side port and located just downstream of the closure disk 24, is used to determine the time required for rupture of the disk 24. This time is referred to a pressure vs. time calibration curve which gives the actual pressure at the closure disk location 24. Time of rupture is exhibited as a discontinuity 1, in the otherwise substantially linear drop in the pressure drop curve shown in FIG. 5. As shown in FIG. 1, transducer 20 located upstream from the closure disk 24 can be used to determine the time of rupture on the side port pressure drop curve in the event that more than one discontinuity occurs on the curve due to, e.g., electrical noise.

Figure 3:
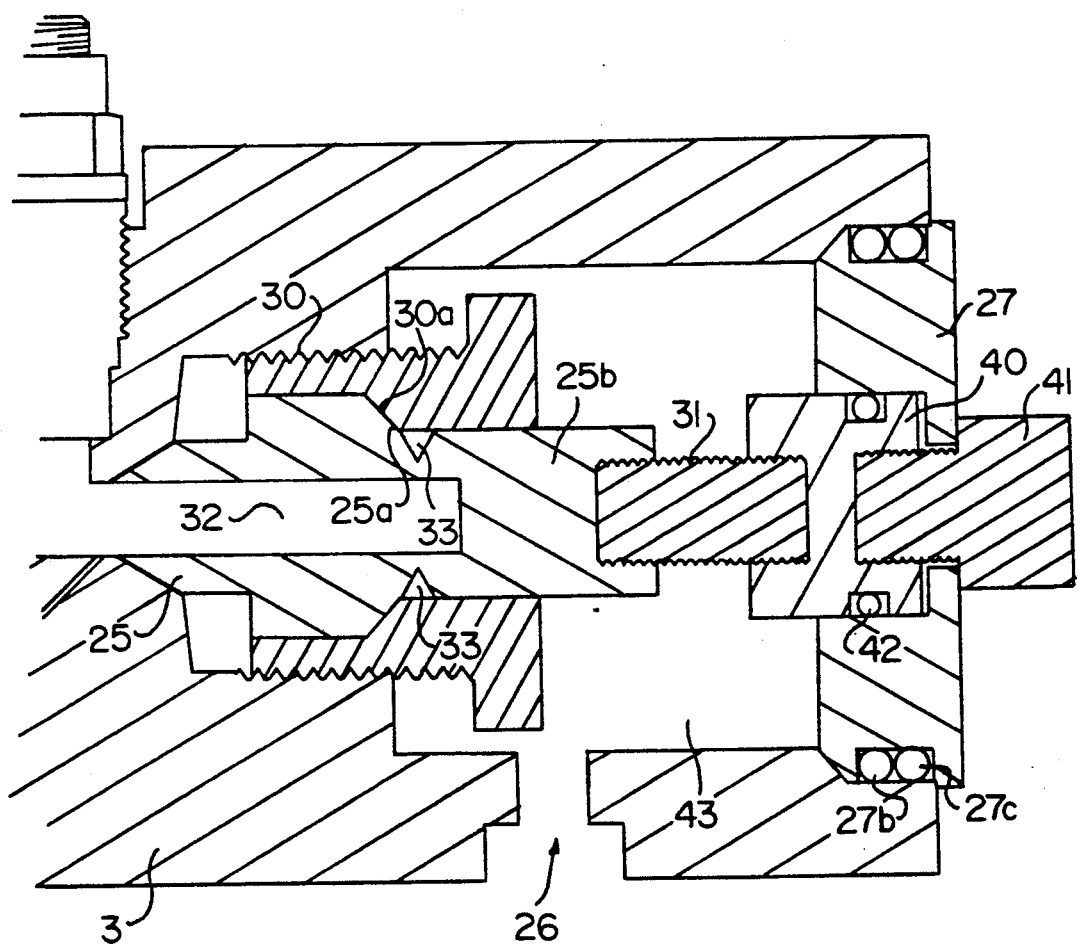
FIG. 3 is a close-up, cross-sectional view of the device of FIG. 1 showing detail of a device for rapidly venting pressure according to the present invention.

Referring to FIG. 1, a high rate of pressure drop on the downstream side 28 of the closure disk 24 is accomplished by rapid venting of high pressure through a high pressure conduit 32 by the rupture of a hollow notched plug 25. As shown in FIG. 3, the hollow notched plug 25 is held in place in the testing device by a gland nut 30. The gland nut 30 has a tapered edge 30a which mates with a tapered edge 25a of the hollow notched plug 25. A notch 33 is provided in the plug to provide an annular rupture area.

The plug may be made of any material which will withstand high pressure yet fracture under a predictable applied axial force. For very high pressures metal plugs are preferred. Metal alloys, e.g., stainless steel, and plastics may also be used. For plastics and other weaker materials a shallower notch may be necessary to prevent rupture at undesirably low pressures. Much stronger materials may require a deeper notch depending upon what pressures are desirable at rupture.

High pressure exerted through the high pressure conduit 32 to the hollow notched plug 25 is not sufficient to rupture the plug 25 at the notch 33. An additional small axial tensile load applied to the end of the plug 25b enables rupture. As shown in FIGS. 1 and 3, this additional load is provided by rapidly pressurizing a cylindrical pressure chamber 43 in which the plug 25 is located. This rapid pressurization acts against a piston 27 fitted in the end of pressure chamber 43. Piston 27 is connected to the hollow notched plug 25 at its end 25b by means of a threaded stud 31 and a sealing means through which the threaded stud 31 and the piston 27 are connected.

The pressure chamber 43 is pressurized by a pressure source connected to a pressure inlet 26. The pressure acts against the piston 27 and through connecting means provides a small axial tensile load to the end 25b of the hollow notched plug 25. Upon application of the small axial tensile load, the hollow notched plug 25 is ruptured annularly along the notch 33 at a very high rate providing a very rapid release of high pressure through the thus formed high pressure conduit 32. Significant mechanical advantages are achieved since the area of the piston 27 against which the pressure acts is much greater than the annular cross-sectional area of the hollow notched plug 25 at the notch 33. The notch provides a stress point at which a crack propagates circumferentially upon application of the axial force provided to the end 25b of the hollow notched plug 25.

Pressures of only about 1000 psi are used to pressurize the pressure chamber 43 through the pressure inlet 26. A standard gas bottle may be used or a branch from the high pressure source with a regulator.

Figure 4:
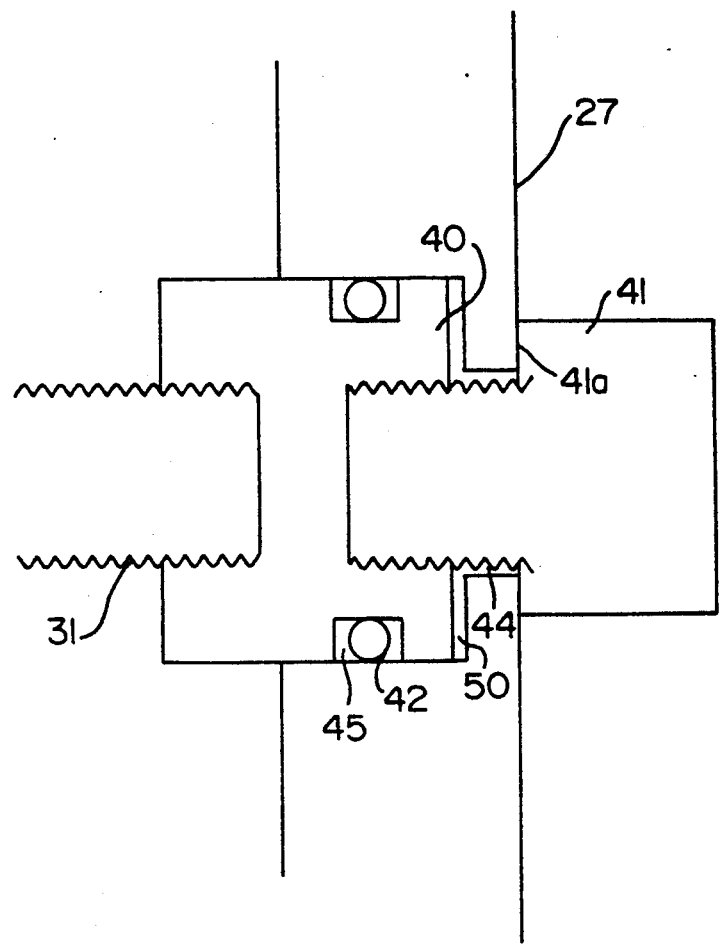
FIG. 4 is a close-up, cross-sectional view of a device for transmission of a tensile load with details of a means providing a seal against the escape of pressure according to an embodiment of the present invention.

Referring to FIGS. 3 and 4, the connecting means which connects the piston 27 to the end 25b of the hollow notched plug 25 comprises a threaded stud 31, a piston plug 40, a tensioning bolt 41, and an O-ring 42. This device provides a transmission of force from the piston 27 to the threaded shaft 31 by applying force to the tensioning bolt 41 at shoulders 41a. The tensioning bolt 41 has threads which engage the piston plug 40 after passing through a hole 44 in the top of the piston 27. Piston plug 40 is fitted within a cylindrical recess 50 in piston 27 centered about hole 44. Blind threaded holes on either side of the piston plug 40 permit transmittal of force from the piston 27 to the end 25b of the hollow notched plug through the tensioning bolt 41, and the threaded stud 31. By turning the tensioning bolt 41, the piston 27 may be drawn into the pressure chamber 43 and attached to the hollow notched plug 25 via the threaded stud 31 without a need to rotate the piston 27 which must be fit tightly in the cylinder.

A means is provided for rotatably sealing the piston plug 40 within recess 50 to permit transmittal of force from the piston 27 to the end 25b of the hollow notched plug 25 without pressure leakage. The means for providing the seal comprises the piston plug 40, the tensioning bolt 41, and an O-ring 42 which mates the piston plug 40 to the piston 27 at recess 50. The O-ring 42 is disposed in a notch 45 formed in the piston plug 40.

Upon application of pressure to the pressure chamber 43 through pressure inlet 26, the piston 27 moves outwardly providing an axial tensile force through the connecting means to the end 25b of the hollow notched plug 25. The axial force is enough to rupture the plug 25 along notch 33. After the plug ruptures, the high pressure exerted through the high pressure conduit 32 forces the end 25b of the plug out of the gland nut 30 to form a venting passage from the high pressure conduit 32 to the pressure chamber 43. The rapid venting of high pressure through this passage provides the rate of change of pressure needed to rupture the closure disk 24 and allow testing of the same. In the event that the piston 27 is forced from the device at high acceleration upon plug rupture, means may be provided to cushion its stoppage.

A new hollow notched plug 25 needs to be loaded into the testing device for each test. After the piston 27 has been forced from the pressure chamber 43 under high pressure, the gland nut 30 is accessible and may be removed. The spent hollow notched plug is replaced with a new hollow notched plug 25 which is secured into the device between the gland nut 30 and a gland nut receptacle in the device body. Tapered edges of the plug 25a and the nut 30a meet to hold the plug 25 in place. The piston is then recovered from the previous test, provided with new piston rings 27b and 27c if necessary, and connected to the end 25b of the hollow notched plug 25 by the connecting means discussed above. The tensioning bolt 41 is tightened to draw the piston 27 into the cylinder 43 without a need to rotate the cylinder. The device is then ready for loading and testing a new closure disk.

EXAMPLE

An initial pressurization of 30,000 psi was provided A stainless steel hollow notched plug was ruptured. The average burst pressure differential was 10,150 psi. The average time required for rupture of the closure disks was 41 microseconds. The rate of pressure drop downstream from the closure disk and prior to rupture averaged 319,000,000 psi/sec. Since increasing the initial pressurization increases the rate of pressure drop, it is expected that increasing the initial pressurization decreases the time required for rupture of the closure disk.

Although the testing device and method have been described in terms of preferred embodiments, it will be appreciated by those skilled in the art that additions, modifications, substitutions and deletions not specifically described may be made without departing from the spirit and scope of the invention as defined in the appended claims.

What is claimed is:

1. A rupturable plug for rapidly venting high pressure from a high pressure source through a conduit formed within said plug, said plug comprising:
    a first segment and a second segment, said first segment being secured to said high pressure source, and said first and second segments having a hollow portion forming said conduit completely through said first segment and terminating in said second segment;
    a notched portion around the circumference of said plug, and defining said first segment from said second segment, said notched portion defining a rupture area; and
    a means within said second segment of said plug for receiving an internal axial force, whereby rupture of said plug at said notched portion is caused by said high pressure and said axial force building within said second segment.

2. A plug as in claim 1, wherein said axial force is a tensile force.

3. A plug for rapidly venting high pressure as in claim 1, wherein said first segment of said plug comprises retaining means to hold said first segment in said high pressure source.

4. A plug as in claim 3, wherein said retaining means comprises a tapered edge.

5. A plug as in claim 2, wherein said second segment of said plug comprises a linking means for mechanically linking said plug to means for providing said tensile force.

6. A plug for rapidly venting high pressure as in claim 5, wherein said linking means includes a threaded hole which receives a threaded stud mechanically linked to said means for providing an axial force.

7. A plug as in claim 1, wherein said plug comprises a metal.

8. A plug as in claim 7, wherein said plug comprises stainless steel.

* * * * *